US009839455B2

(12) United States Patent
Cole

(10) Patent No.: US 9,839,455 B2
(45) Date of Patent: *Dec. 12, 2017

(54) BONE FIXATION SYSTEM AND METHOD OF USE

(71) Applicant: J. Dean Cole, Orlando, FL (US)

(72) Inventor: J. Dean Cole, Orlando, FL (US)

(73) Assignee: J. Dean Cole, Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/826,044

(22) Filed: Aug. 13, 2015

(65) Prior Publication Data

US 2015/0342651 A1    Dec. 3, 2015

Related U.S. Application Data

(60) Continuation of application No. 12/904,815, filed on Oct. 14, 2010, now Pat. No. 9,107,701, which is a
(Continued)

(51) Int. Cl.
*A61B 17/72* (2006.01)
*A61B 17/80* (2006.01)
*A61B 17/68* (2006.01)

(52) U.S. Cl.
CPC ........ *A61B 17/7241* (2013.01); *A61B 17/683* (2013.01); *A61B 17/72* (2013.01);
(Continued)

(58) Field of Classification Search
CPC .... A61B 17/72; A61B 17/725; A61B 17/7291
See application file for complete search history.

(56) References Cited

U.S. PATENT DOCUMENTS 2,765,787 A    10/1956 Pellet
2,952,254 A    9/1960 Keating
(Continued)

FOREIGN PATENT DOCUMENTS

DE    29719293 U1    2/1998
JP    2002-511281    4/2002
(Continued)

OTHER PUBLICATIONS

European Patent Office, "Examination report" for Application No. 14002127.0, dated Jun. 21, 2016, 4 pages.
(Continued)

*Primary Examiner* — Nicholas Woodall
(74) *Attorney, Agent, or Firm* — Haynes and Boone, LLP

(57) ABSTRACT

An apparatus includes: a member configured to be received within an intramedullary canal of a fibula, the member having an opening therethrough; a bone plate including a first bone-engaging surface; a flexible elongate element having a first portion, a second portion, and a third portion, at least the second and third portions being sized to extend through the opening of the member, wherein the second portion is movable by bending of the flexible elongate element between an insertion position and a bone-engaging position, wherein the second portion is configured to extend through the opening of the member while the second portion is in the insertion position, and wherein the second portion includes a second bone-engaging surface while the second portion is in the bone-engaging position; and a coupling structure for operatively coupling the bone plate to the first portion of the flexible elongate element.

17 Claims, 7 Drawing Sheets

Related U.S. Application Data division of application No. 11/461,502, filed on Aug. 1, 2006, now Pat. No. 7,963,966.

(52) U.S. Cl.
CPC ........ *A61B 17/725* (2013.01); *A61B 17/7233* (2013.01); *A61B 17/809* (2013.01); *A61B 17/8061* (2013.01); *A61B 2017/681* (2013.01)

(56) References Cited

U.S. PATENT DOCUMENTS

| | | |
|---|---|---|
| 3,439,671 A | 4/1969 | Kuntscher |
| 3,763,855 A | 10/1973 | McAtee |
| 4,212,294 A | 7/1980 | Murphy |
| 4,741,330 A | 5/1988 | Hayhurst |
| 5,041,129 A | 8/1991 | Hayhurst et al. |
| 5,098,433 A | 3/1992 | Freedland |
| 5,167,666 A | 12/1992 | Mattheck et al. |
| 5,248,313 A | 9/1993 | Greene et al. |
| 5,529,075 A | 6/1996 | Clark |
| 5,601,557 A | 2/1997 | Hayhurst |
| 5,989,256 A | 11/1999 | Kuslich et al. |
| 6,010,505 A | 1/2000 | Asche et al. |
| 6,019,762 A | 2/2000 | Cole |
| 6,068,648 A | 5/2000 | Cole et al. |
| 6,358,250 B1 | 3/2002 | Orbay |
| 6,547,793 B1 | 4/2003 | McGuire |
| 6,719,801 B1 | 4/2004 | Holt |
| 6,761,722 B2 | 7/2004 | Cole et al. |
| 6,902,573 B2 | 6/2005 | Strobel et al. |
| 7,837,717 B2 | 11/2010 | Deffenbaugh et al. |
| 7,963,980 B1 | 6/2011 | Freeman et al. |
| 2002/0055743 A1 | 5/2002 | Seemann |
| 2003/0135212 A1 | 7/2003 | Chow |
| 2003/0236555 A1 | 12/2003 | Thornes |
| 2005/0149025 A1 | 7/2005 | Ferrante et al. |
| 2005/0283154 A1 | 12/2005 | Orbay et al. |

FOREIGN PATENT DOCUMENTS

| | | |
|---|---|---|
| JP | 2005-509480 | 4/2005 |
| WO | WO 98/35623 | 8/1998 |
| WO | WO99/37219 | 7/1999 |

OTHER PUBLICATIONS

United States Patent Office, International Searching Authority, Notification of Transmittal of the International Search Report and the Written Opinion of the International Searching Authority or the Declaration, International Application No. PCT/US07/74832, dated Jul. 3, 2008, 6 pages.

Supplementary European Search Report received in European Application No. 07813582. 9, dated Sep. 24, 2012, 7 pages.

Japanese Patent Office, "Office Action," for Japanese Application No. 2009-523013, dated Jun. 5, 2012, 12 pages including translation.

European Patent Office, "European Search Report and Written Opinion," for European application No. 14002127.0, dated Sep. 18, 2014, 8 pages.

European Patent Office, "Examination Report" for Application No. 14 002 127.0-1664, dated Mar. 23, 2017, 5 pages.

Japanese Patent Office, Office Action, for Japanese Application No. 2013-245864, dated Apr. 25, 2017, 10 pages with translation.

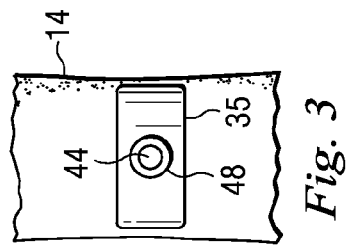
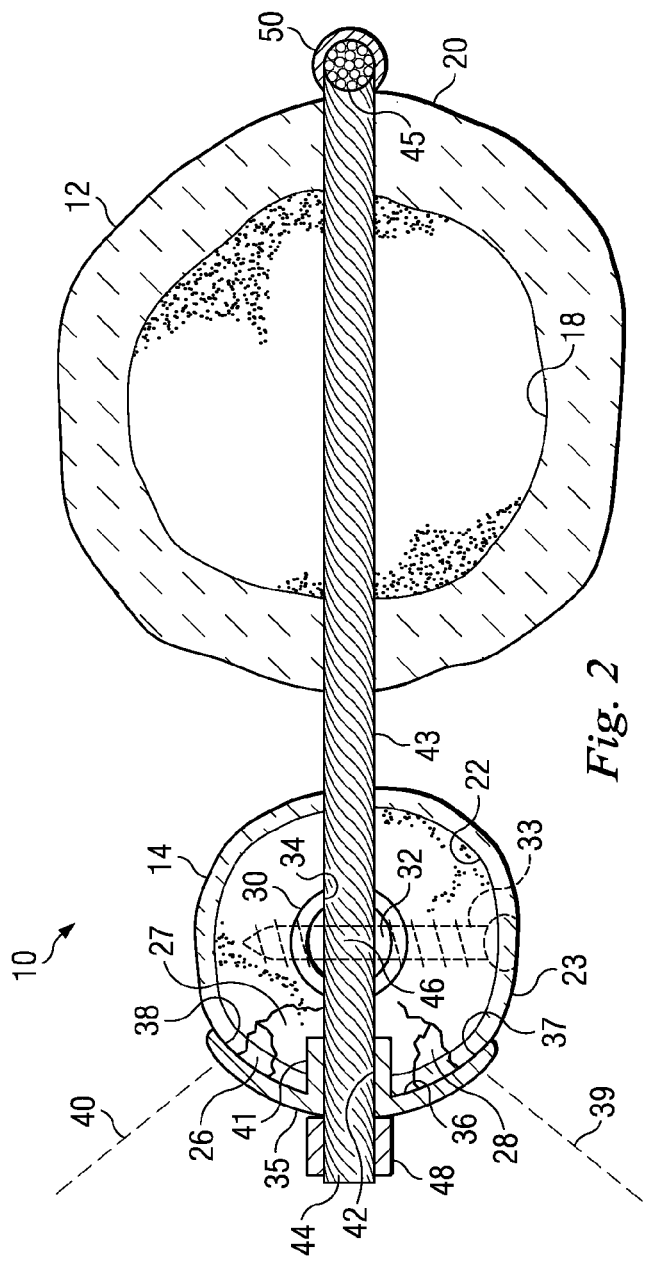

BONE FIXATION SYSTEM AND METHOD OF USE

CROSS REFERENCE TO RELATED APPLICATIONS

This application is a Continuation application of U.S. patent application Ser. No. 12/904,815, filed Oct. 14, 2010, now U.S. Pat. No. 9,107,701, which is a Divisional application of U.S. patent application Ser. No. 11/461,502, filed Aug. 1, 2006, now U.S. Pat. No. 7,963,966, the disclosures of which are incorporated herein by reference in their entireties.

BACKGROUND

Embodiments of the present disclosure relate generally to devices and methods for accomplishing bone fixation, and more particularly in some embodiments, to devices and methods for reduction and fixation of a type IV supination external rotation injury.

The treatment of fractures in the femur, tibia, fibula, and other bones often requires reduction and fixation of the bone. Further, for some injuries it is also helpful, or necessary, to limit the motion between the fractured bone and another bone. For example, in the treatment of a type IV supination external rotation injury, limiting but not completely preventing syndesmotic motion between the fibula and tibia can be advantageous. Although existing methods, devices, and surgical techniques have been generally adequate for their intended purposes, they have not been entirely satisfactory in all respects.

BRIEF DESCRIPTION OF THE DRAWINGS

FIG. 2 is a sectional view of the arrangement of FIG. 1 taken along section line 2-2.

FIG. 3 is a diagrammatic, fragmentary side view of the arrangement of FIG. 1.

DETAILED DESCRIPTION

Figure 1:
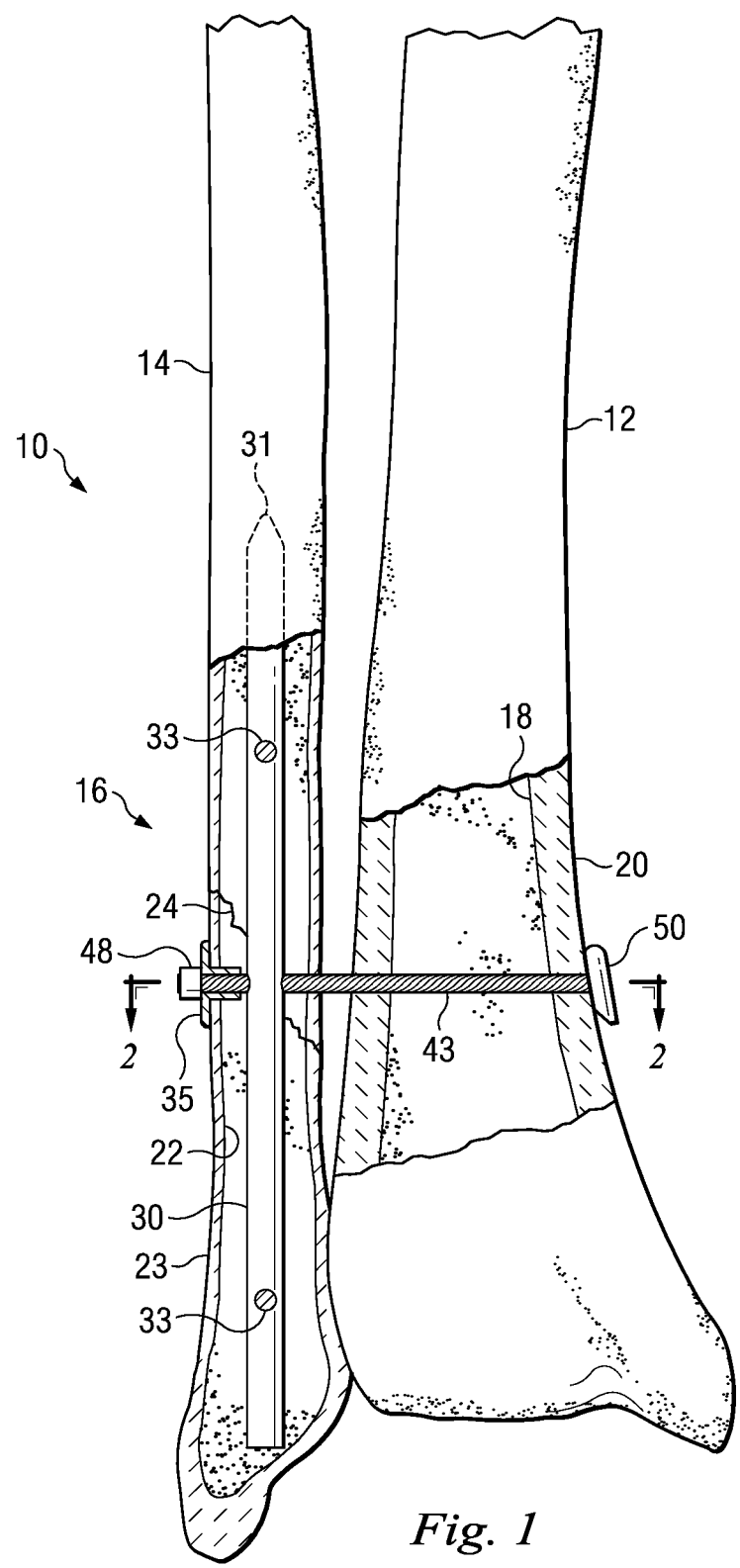
FIG. 1 is a diagrammatic fragmentary front view of an arrangement that embodies aspects of the present invention.

FIG. 1 is a diagrammatic fragmentary front view of an arrangement 10 that embodies aspects of the present invention. The arrangement 10 includes a bone 12, a bone 14, and an apparatus 16. FIG. 2 is a sectional view of the arrangement 10 of FIG. 1 taken along section line 2-2.

In the embodiment shown in FIG. 1, the bones 12 and 14 are parts of a human leg, where the bone 12 is a tibia and the bone 14 is a fibula. The bone 12 has intramedullary canal 18 and an exterior surface 20. Similarly, the bone 14 has an intramedullary canal 22 and an exterior surface 23. The bone 14 also has a fracture 24. As best shown in FIG. 2, the fracture 24 has caused the bone 14 to have several bone fragments, some of which are visible at 26, 27, and 28.

As shown in FIGS. 1 and 2, the apparatus 16 includes a member or intramedullary rod 30. The intramedullary rod 30 is approximately cylindrical and configured to be received within the intramedullary canal 22 of the bone 14. In the embodiment shown in FIG. 1, the intramedullary rod 30 includes a tapered portion 31 at its upper end that facilitates insertion of the intramedullary rod into the intramedullary canal 22. As best shown in FIG. 2, the intramedullary rod 30 includes a central, longitudinal opening 32. The opening 32 opens through the lower end of the intramedullary rod 30 and extends substantially the entire length of the intramedullary rod to a location near the upper end. The intramedullary rod 30 is made of a sturdy, surgical-grade material, and in particular is made of stainless steel. Two fixation members or bone screws 33 pass through respective, axially spaced, transverse, parallel openings in the intramedullary rod 30 to secure the rod to the bone 14, as shown in FIG. 1. The transverse openings extend completely through the intramedullary rod 30 in a generally anterior to posterior direction. In the embodiment of FIG. 1, the bone screws 33 are made of stainless steel. As best illustrated in FIG. 2, the intramedullary rod 30 also includes a further transverse opening 34 located between the openings for bone screws 33 and extending in a generally lateral to medial direction. The opening 34 extends completely through the rod 30 and is angularly offset by approximately 90° with respect to the openings the bone screws 33 pass through.

The apparatus 16 also includes an anchor 35. The anchor 35 includes a curved, plate-like portion with a bone-engaging surface 36. As best shown in FIG. 2, the bone-engaging surface 36 is curved to approximately match the curvature of the exterior surface 23 of the bone 14. Thus, the bone-engaging surface 36 has a concave surface that engages the bone 14. In the illustrated embodiment, the concave surface is approximately cylindrical and oriented so that it extends parallel to the longitudinal axis of bone 14. The bone engaging surface 36 of the anchor 35 engages the exterior surface 23 of the bone 14 adjacent the bone fragments 26-28. The bone-engaging surface includes a plurality of spaced surface portions that apply forces to the bone 14 in respective, different directions. By way of example, two of these surface portions are shown at 37 and 38 in FIG. 2. The spaced surface portions 37 and 38 apply respective forces in directions parallel to an axis 39 and an axis 40. The axes 39 and 40 are at an angle with respect to one another. As shown best in FIG. 2, the anchor 35 also includes a projection 41 that projects outwardly from a central region of the surface 36. The projection 41 is approximately cylindrical and extends into the bone 14. A central longitudinal opening 42 in the projection 41 extends completely through the anchor 35. The anchor 35 is made of a flexible, surgical-grade material, and in particular is made of cobalt-chrome. FIG. 3 is a diagrammatic, fragmentary side view of the arrangement 10 of FIG. 1. As shown, the plate-like portion of the anchor 35 is approximately rectangular in shape with rounded corners.

Referring again to FIGS. 1 and 2, the apparatus 16 also includes a flexible elongate element or cable 43. The cable 43 is formed from flexible surgical-grade material, and in particular is made of cobalt-chrome. The cable 43 includes a portion 44, a portion 45, and a portion 46. In the embodiment shown in FIGS. 1 and 2, the portions 44-46 of the cable 43 are of a substantially uniform diameter, and the cable 43 extends through the opening in the anchor 35, the opening 34 in the intramedullary rod 30, and portions of both of the bones 12, 14. The cable 43 is substantially taut, but can flex. A ferrule 48 is fixedly secured to the portion 44 by crimping the ferrule to the cable 43. The ferrule 48 is formed from a deformable surgical-grade material, and in particular is made of cobalt-chrome.

Figure 4:
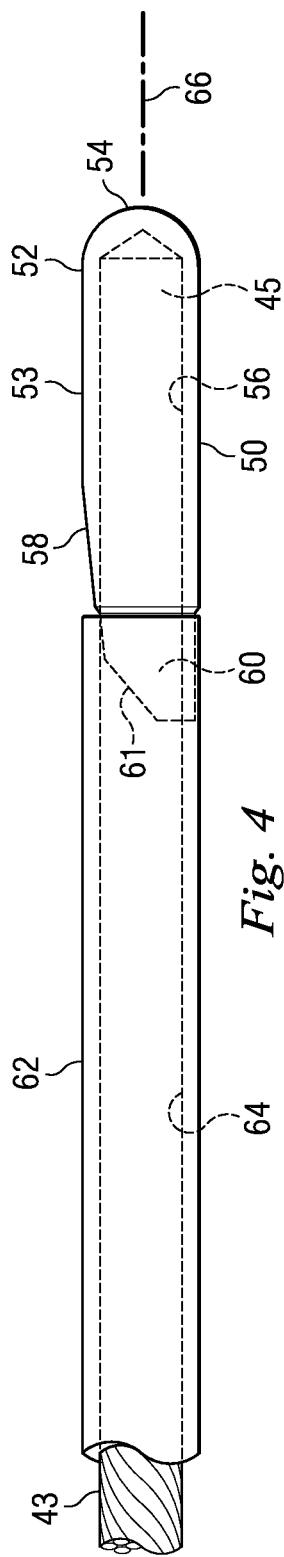
FIG. 4 is a diagrammatic fragmentary front view of selected components of the apparatus 16 of FIG. 1 in one operational position, and also shows part of a delivery device.
Figure 5:
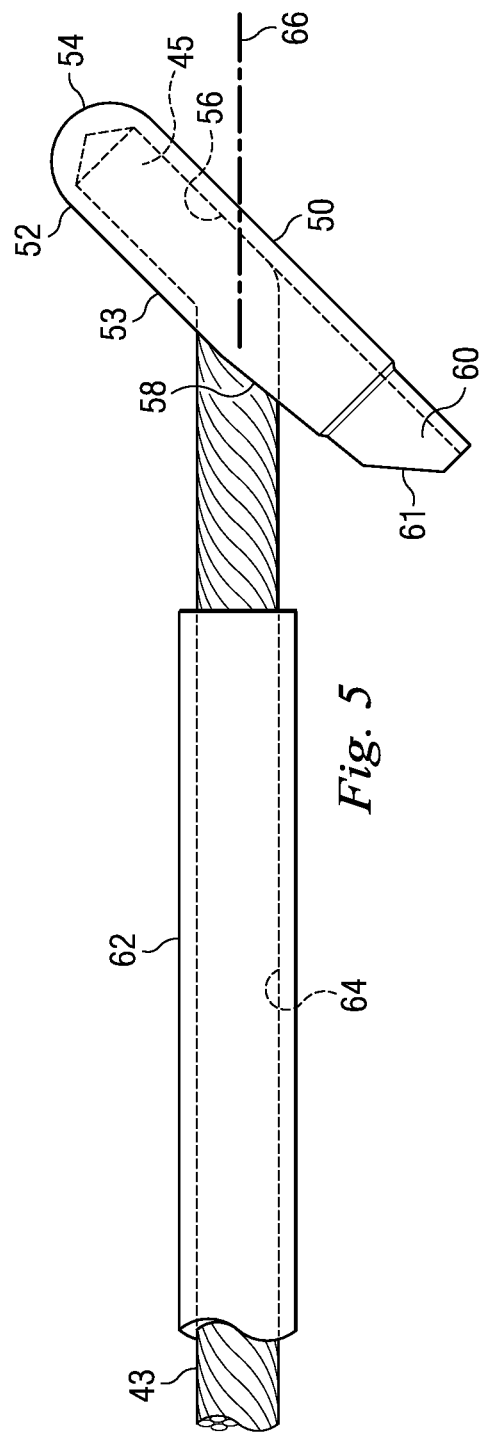
FIG. 5 is a diagrammatic fragmentary front view, similar to FIG. 4, but showing a different operational position.

A mechanism 50 is coupled to the portion 45. FIG. 4 is a diagrammatic fragmentary front view of selected components of the apparatus 16 of FIG. 1 in one operational position, and also shows a portion 62 of a delivery device. FIG. 5 is a diagrammatic fragmentary front view, similar to FIG. 4, but showing a different operational position.

The mechanism 50 includes a section 52. The section 52 includes a bone-engaging surface 53. The section 52 is approximately cylindrical, has a rounded end surface 54, and has an central longitudinal opening 56. The opening 56 opens through the end of section 52 remote from surface 54 and extends to a location near surface 54. The opening 54 has a diameter that is approximately the same as the outer diameter of the cable 43. The end of section 52 near surface 54 is crimped to the end of cable portion 45 to couple the mechanism 50 to the cable 43. The flexible nature of the cable 43 serves to permit limited pivotal movement of the mechanism 50 relative to the cable. The end of the portion 45 of the cable is bent to the position shown in FIG. 5. The portion 45 is deformable to other positions, as shown in FIG. 4, but is resilient such that it returns to the bent position shown in FIG. 5. The section 52 also includes a slot 58 through a sidewall having the bone-engaging surface 53 thereon. The slot 58 communicates with the opening 54 and extends axially from the left end of section 52, as seen in FIG. 4, approximately half the length of section 52. The section 52 also includes an end portion 60. The end portion 60 is approximately cylindrical with a diameter less than the outer diameter of section 52. The end portion 60 also includes an inclined surface 61 that extends at an angle with respect to a longitudinal axis of section 52. In the current embodiment, the section 52 is made of cobalt chrome.

In FIGS. 4 and 5, the cable 43 and coupling mechanism 50 are shown in combination with a cannula 62 that is part of a delivery device. The cannula 62 is made of a surgical-grade material, and in particular stainless steel. The cannula 62 is cylindrical with an opening 64 extending along its entire length. In the current embodiment, the diameter of the opening 64 is slightly larger than the outer diameter of the cable 43, such that the cable 43 is slidable within the opening. Further, the diameter of the opening 64 is such that the end portion 60 of section 52 fits within the cannula, as shown in FIG. 4.

The section 52 is moveable between two positions: an insertion position wherein the section 52 is approximately parallel with a longitudinal axis 66 of the cable 43 (as shown in FIG. 4), and a bone-engaging position wherein the section 52 is at an angle with respect to the longitudinal axis 66 of the cable (as shown in FIGS. 1 and 2). The bend in the cable 43 resiliently biases the section 52 toward the bone-engaging position. The slot 58 receives a piece of the cable 43 when the section 52 is in the bone-engaging position so that the section 52 can pivot with respect to the longitudinal axis of the cable.

The apparatus 16 is utilized for reduction and fixation of the fracture 24 and for limiting syndesmotic motion between the bones 12, 14. The apparatus 16 is assembled and implanted in the following manner. The intramedullary rod 30 is installed within the intramedullary canal 22 of the bone 14 extending across fracture 24 using known techniques. The intramedullary rod 30 is secured in place by bone screws 33. Once secured in place, the intramedullary rod 30 helps to align and stabilize the fracture 24.

Figure 6:
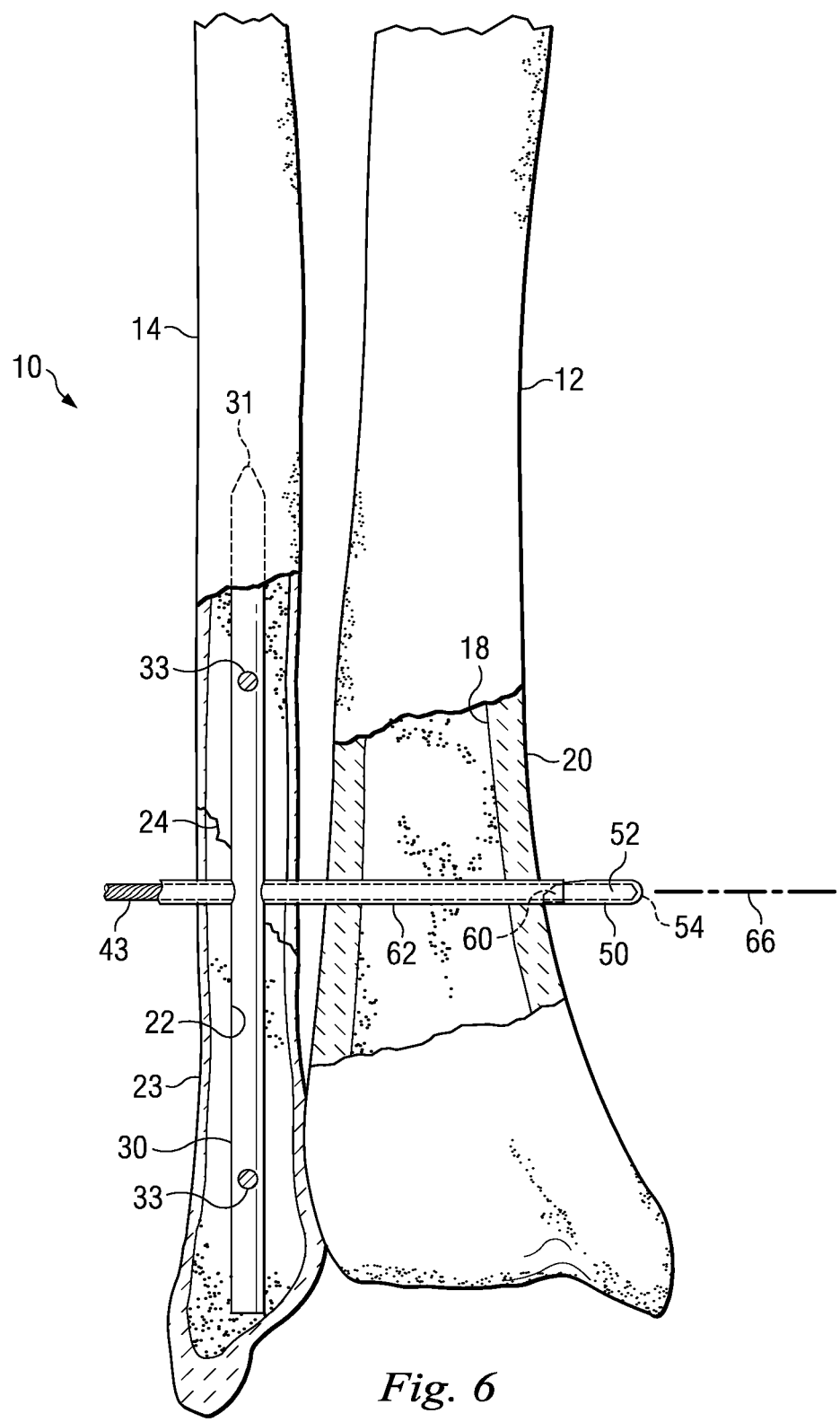
FIG. 6 is a diagrammatic, fragmentary front view of several of the components of the arrangement of FIG. 1 in a partially assembled state.

FIG. 6 is a diagrammatic, fragmentary front view of several of the components of the arrangement 10 of FIG. 1 in a partially assembled state. Referring to FIG. 6, the cable 43 is shown in the process of being inserted from a lateral approach to fibula 14. The cable 43 passes through cannula 62 and is securely coupled to the mechanism 50 at one end. The end portion 60 is received within the cannula 62 to hold the section 52 in the installation position during insertion. The cannula 62 cooperates with the mechanism 50 such that as the cannula is advanced forward, the mechanism 50 and, therefore, the cable 43 are also advanced forward. The rounded tip 54 of the mechanism 50 serves to guide the cable 43 and cannula 62 through opening 34 of rod 30 and through portions of bones 12 and 14. In the current embodiment, a drill is used to form a passage through bones 12 and 14 in alignment with opening 34 prior to insertion of the cannula 62.

Figure 7:
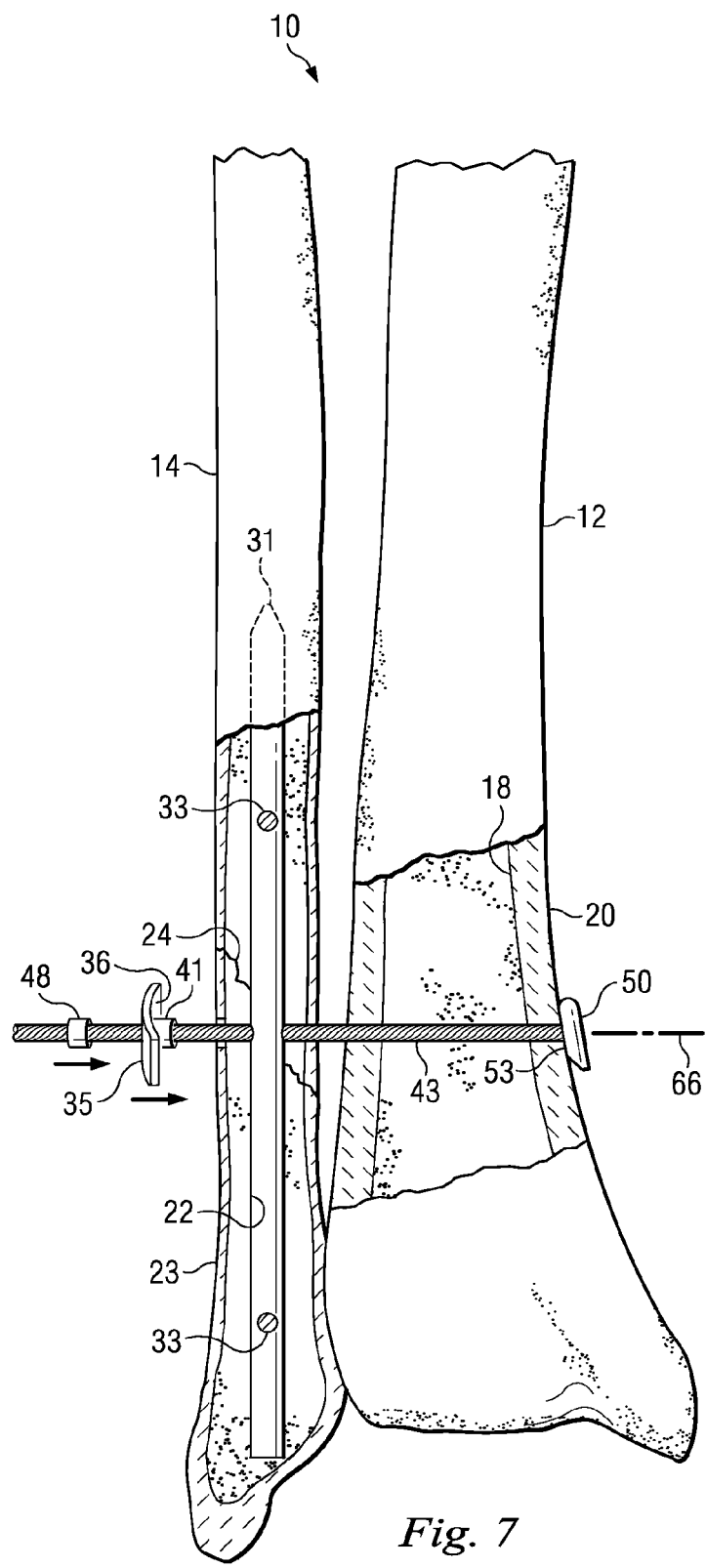
FIG. 7 is a diagrammatic, fragmentary front view of the arrangement of FIG. 1 in a partially assembled state.

FIG. 7 is a diagrammatic, fragmentary front view of the arrangement 10 of FIG. 1 in a partially assembled state. Once the mechanism 50 has passed all the way through bone 14, across the gap between the bone 12 and bone 14, and all the way through bone 12, the section 52 is moved from the insertion position—in substantial alignment with the longitudinal axis 66 of the cable 43, as shown in FIG. 6—into the bone-engaging position—at an angle with respect to the longitudinal axis 66 of the cable, as shown in FIG. 7. As previously mentioned, the cable 43 is bent such that it resiliently biases the section 52 toward the bone-engaging position. Thus, moving the section 52 between the insertion position and the bone-engaging position is accomplished by either retracting the cannula 62 with respect to the cable 43 or extending the cable with respect to the cannula. The inclined surface 61 facilitates movement of the section 52 between the insertion position and the bone-engaging position by allowing the end portion 60 to be more easily removed from the cannula 62 and rotated into the bone-engaging position. The cannula 62 is removed once the section 52 is in the bone-engaging position.

Referring to FIG. 7, once the section 52 is inserted and rotated into the bone-engaging position, the bone-engaging surface 53 abuts the exterior surface 20 of bone 12. Engagement of the exterior surface 20 and the bone-engaging surface 53 prevents leftward lateral movement of the cable 43, as viewed in FIG. 7. This also allows the cable 43 to be tensioned. FIG. 7 shows the anchor 35 and the uncrimped ferrule 48 slidably supported on the cable 43. The anchor 35 is moved rightwardly along the cable 43 until the projection 41 is positioned within at least a portion of the bone 14. The bone-engaging surface 36 initially engages the exterior surface 23 of the bone 14 adjacent the bone fragments 26-28 (FIG. 2). As the anchor 35 is moved into position, the bone-engaging surface 36 is urged against the bone fragments and helps to reduce the fracture 24. Once in position, the bone-engaging surface 36 functions to properly align and hold the bone fragments in place. The ferrule 48 is then advanced rightwardly along the cable 43 to a position adjacent the anchor 35. The left end of the cable 43 is pulled leftwardly in FIG. 7 to tension the cable, and the ferrule 48 is pressed rightwardly and then crimped to the cable 43. Once the ferrule 48 is crimped to the cable 43, the end of portion 44 of the cable is cut so that it does not extend beyond the ferrule 48, as shown in FIGS. 1 and 2. Since the cable 43 is tensioned before crimping the ferrule 48, the anchor 35 will be held securely in place with respect to the exterior bone surface 23 and the bone fragments. Further, the tension along cable 43 also serves to limit or stabilize the motion between the bones 12 and 14. The flexibility of the cable 43 allows some limited syndesmotic motion. Thus, the apparatus 16 is able to simultaneously reduce and fix the fracture 24 and limit syndesmotic motion between the bones 12 and 14.

The components of the apparatus 16, including the intramedullary rod 30, the bone screws 33, the anchor 35, the cable 43, the ferrule 48, and the coupling mechanism 50, have been described as being made from certain specific surgical-grade materials including stainless steel and cobalt-chrome. However, these components can alternatively be made of other appropriate surgical-grade materials, including: metals, such as titanium and titanium alloys; polymers, such as polyetheretherketone (PEEK); or any other suitable materials. Further, the materials chosen may be based on a desired flexibility, or lack thereof, for the specific component. Further, the actual shapes, sizes, and material choices for the various components may be varied, and for example modified for the particular application or patient.

Figure 8:
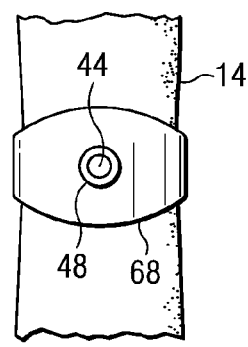
FIG. 8 is a diagrammatic, fragmentary side view similar to FIG. 3, but showing an alternative embodiment.
Figure 9:
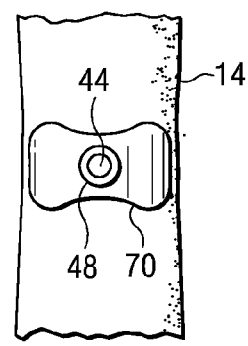
FIG. 9 is a diagrammatic, fragmentary side view similar to FIG. 3, but showing an alternative embodiment.

For example, FIG. 8 is a diagrammatic, fragmentary side view similar to FIG. 3, but showing an anchor 68 that is an alternative embodiment of the anchor 35 of FIG. 3. The anchor 68 is similar to the previously described anchor 35, except that the anchor 68 has curved upper and lower edges, as shown. FIG. 9 is a diagrammatic, fragmentary side view similar to FIG. 3, but showing an anchor 70 that is an alternative embodiment of the anchor 35 of FIG. 3. The anchor 70 is similar to anchor 35, except that the anchor 70 has a curved, "hour-glass" shape with smooth contours, as shown.

Figure 10:
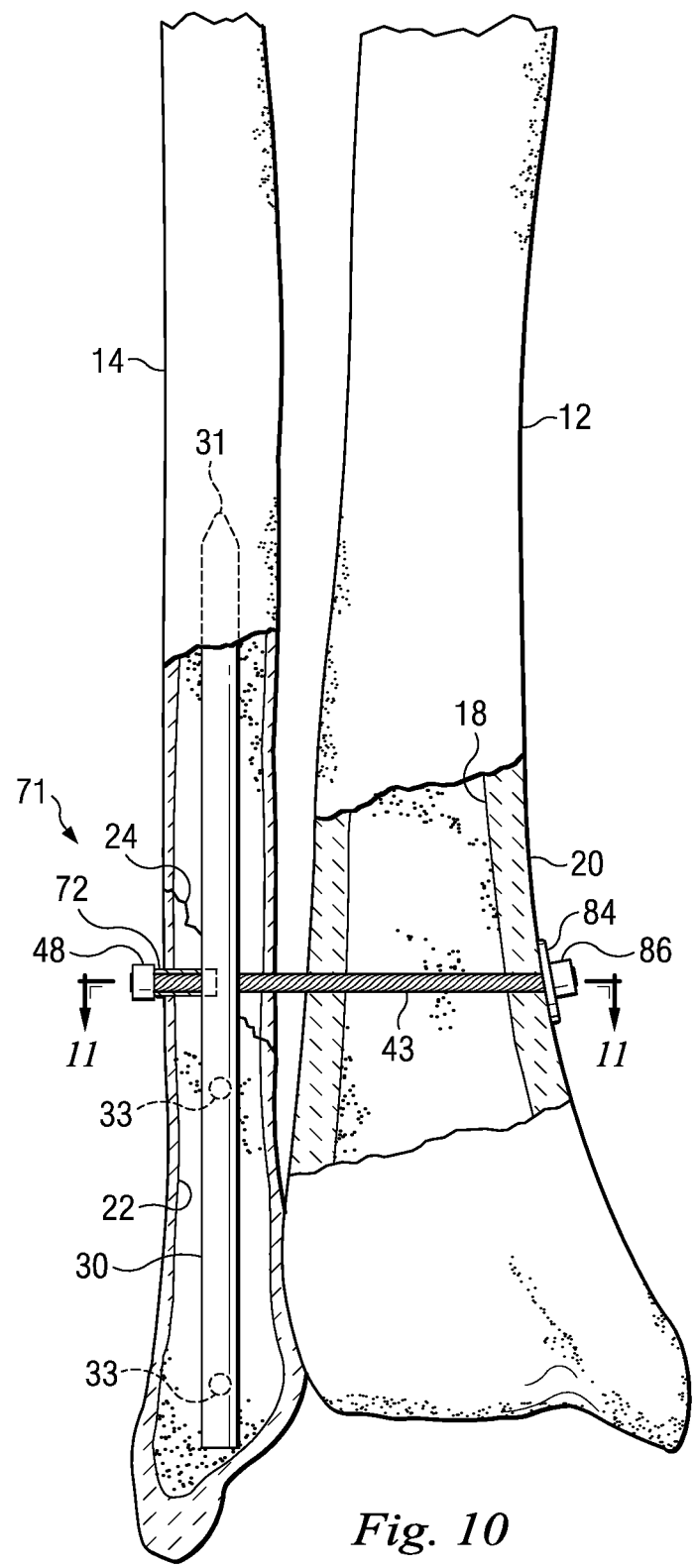
FIG. 10 is a diagrammatic fragmentary front view similar to FIG. 1, but showing an alternative embodiment.
Figure 11:
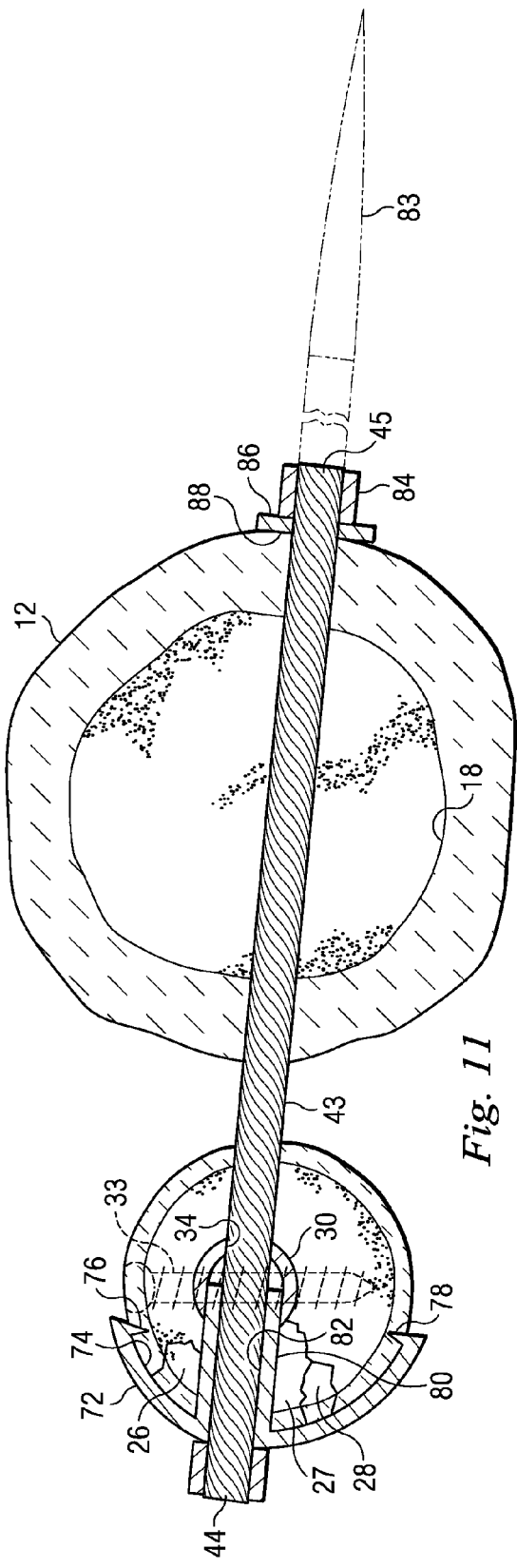
FIG. 11 is a sectional view of the alternative embodiment shown in FIG. 10 taken along section line 11-11.

FIG. 10 is a diagrammatic, fragmentary front view similar to FIG. 1, but showing an apparatus 71 that is an alternative embodiment of the apparatus 16. FIG. 11 is a sectional view of the apparatus 71 of FIG. 10 taken along section line 11-11. The apparatus 71 shown in FIGS. 10 and 11 is similar to the apparatus 16 described above, except for the differences noted below.

As shown in FIGS. 10 and 11, the apparatus 71 includes an anchor 72. The anchor 72 includes a curved portion with a bone-engaging surface 74. As best shown in FIG. 11, the bone-engaging surface 74 is curved to approximately match the curvature of the exterior surface 23 of the bone 14. Thus, the bone-engaging surface 74 has a concave surface that engages the bone 14. In the illustrated embodiment, the concave surface is approximately cylindrical and oriented so that its axis extends parallel to the longitudinal axis of bone 14. The bone engaging surface 74 of the anchor 72 engages the exterior surface 23 of the bone 14 adjacent the bone fragments 26-28. The anchor 72 includes barbs 76 and 78 at each end. The barbs 76 and 78 extend from the bone engaging surface 74 at an acute angle generally toward the center of the anchor, as shown. Also, the barbs 76 and 78 are pointed to facilitate engagement with the bone 14. The barbs 76 and 78 serve to secure the anchor 72 against the exterior surface 23 of the bone 14 and hold the bone fragments 26-28 in place for proper reduction of the fracture 24. The angle of the barbs 76 and 78, however, allows the anchor 72 to be urged into position around the bone 14 without interference from the barbs. Once in position the barbs 76 and 78 engage the bone 14 to hold the anchor in place and prevent the anchor 72 from migrating out of position away from the bone fragments 26-28 or the bone 14.

As shown best in FIG. 11, the anchor 72 also includes a projection 80 that projects outwardly from a location eccentric to the center of the surface 74. The projection 80 is approximately cylindrical and extends into the bone 14. The off-center projection 80 is adapted to engage the opening 34 of the intramedullary rod 30. The off-center projection 80 is utilized where the intramedullary rod has been inserted in the intramedullary canal 22 of the bone 14 in an off-center position. FIG. 11 shows the projection 80 engaging the opening 34 where the intramedullary rod 30 has been inserted in a position posterior to a central position. A central longitudinal opening 82 in the projection 80 extends completely through the anchor 72.

Referring again to FIGS. 10 and 11, the apparatus 71 also includes a flexible elongate element or cable 43. In the current embodiment, the portions 44-46 of the cable 43 are of a substantially uniform diameter. The cable 43 is inserted using a needle 83 having a diameter substantially similar to the diameter of the cable portions 44-46. The cable 43 extends through the opening 82 in the anchor 72, the opening 34 in the intramedullary rod 30, portions of both of the bones 12, 14, and the gap between the bones. Adjacent the anchor 72, a ferrule 48 is fixedly secured to the portion 44 by crimping the ferrule to the cable 43. The ferrule 48 is formed from a deformable surgical-grade material, and in particular is made of cobalt-chrome. At the other end of the cable, a ferrule 84, similar to ferrule 48, is fixedly secured to the portion 45 by crimping the ferrule 84 to the cable. A washer 86 is positioned around the cable between the ferrule 84 and the bone 12 to prevent the ferrule and portion 45 of the cable 43 from moving medially beyond the exterior surface 20 of the bone 12. To that end, the washer 86 includes a flat bone-engaging surface 88. The washer 86 is formed from cobalt chrome, such that it is slightly deformable to adapt to the contour of the exterior surface 20 of the bone 12.

Figure 12:
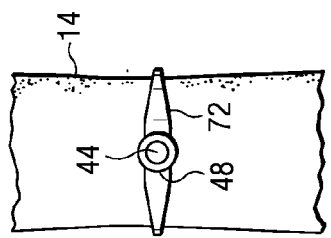
FIG. 12 is a diagrammatic, fragmentary side view of the alternative embodiment of FIG. 10.

FIG. 12 is a diagrammatic, fragmentary side view of the apparatus 71 of FIG. 10. As shown, the anchor 71 is elongate and has tapered ends. The central longitudinal opening 82 has a diameter slightly larger than the diameter of the cable 43 to allow the cable to pass through it.

In some embodiments the anchor 35 is slightly flexible or deformable. In that respect, in some embodiments the anchor 35 is flexible near each end and rigid, or less flexible, near its middle. In a further embodiment, the bone engagement surface 36 of the anchor 35 is substantially circular. Further, in other embodiments the bone-engaging surface 36 may have a variable radius of curvature. Also, in other embodiments the anchor 35 may not include a barrel portion or projection 41. Further, in other embodiments the number of bone screws may be increased or decreased, the orientation of the bone screws may be altered, and the position of the bone screws may be changed. The tension and flexibility of the cable 43 may be adjusted for the particular application or patient, as well. Also, the section 52 may be moved into the bone-engaging position while located in the intramedullary canal 18 of the bone 12. Using such an approach, the bone-engaging surface 53 engages a surface on the cortical bone material surrounding the intramedullary canal 18.

Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An apparatus for fixing a tibia to a fibula while preserving syndesmotic motion therebetween, comprising:
   a member configured to be received within an intramedullary canal of a fibula, the member having an opening therethrough;
   a bone plate including a first bone-engaging surface configured to engage an exterior bone surface of the fibula;
   a flexible elongate element having a first portion, a second portion, and a third portion extending between the first and second portions, at least the second and third portions being sized to extend through the opening of the member, wherein the second portion is movable by bending of the flexible elongate element between an insertion position and a bone-engaging position, wherein the second portion is configured to extend through the opening of the member while the second portion is in the insertion position, and wherein the second portion includes a second bone-engaging surface configured to engage an exterior bone surface of a tibia while the second portion is in the bone-engaging position;
   a coupling structure for operatively coupling the bone plate to the first portion of the flexible elongate element; and
   wherein the flexible elongate element in configured to extend between the fibula and the tibia and has flexibility to limit but not completely prevent syndesmotic motion between the fibula and the tibia.

2. The apparatus of claim 1, wherein the first bone-engaging surface is concave.

3. The apparatus of claim 1, wherein the second bone-engaging surface is substantially flat.

4. The apparatus of claim 1, wherein the member is elongate and the opening extends in a direction substantially transverse to a length of the member.

5. The apparatus of claim 1, wherein the bone plate further includes a projection extending from the first bone-engaging surface and a further opening extending through the projection, the projection configured to extend into the fibula, wherein at least the second and third portions of the flexible elongate element are sized to extend through the further opening.

6. The apparatus of claim 5, wherein:
   the first bone-engaging surface includes spaced first and second surface portions configured to engage the exterior bone surface of the fibula, the first surface portion being configured to exert a first force in a first direction and the second surface portion being configured to exert a second force in a second direction, the first and second directions forming a first angle with respect to each other; and
   the projection including an external surface configured to engage an internal portion of the fibula, the external surface of the projection extending continuously from the first and second surface portions at a second angle relative to the first and second surface portions.

7. The apparatus of claim 5, wherein the first coupling structure includes a ferrule configured to be crimped to the first portion of the flexible elongate element.

8. The apparatus of claim 7, wherein:
   the bone plate and the second portion of the flexible elongate element are oriented so that the first and second bone-engaging surfaces face approximately toward each other, and so that the projection extends from the bone plate toward the second portion of the flexible elongate element; and
   the ferrule of the first coupling structure is crimped to the first portion of the flexible elongate element on a side of the bone plate remote from the second portion of the flexible elongate element.

9. The apparatus of claim 5, wherein the projection is adapted to extend at least partially into the opening of the member.

10. The apparatus of claim 1, wherein the fixation plate includes an opening therethrough, and wherein the anchor is configured to pass through the opening while in the insertion configuration.

11. The apparatus of claim 10, wherein the fixation plate includes a projection adapted to extend into a bone, wherein the opening extends through the projection.

12. The apparatus of claim 11, wherein the projection extends from the first bone-engaging surface and includes an external surface configured to engage an internal portion of the bone.

13. The apparatus of claim 12, wherein:
   the first bone-engaging surface includes spaced first and second portions configured to engage the first exterior bone surface, the first portion being configured to exert a first force in a first direction and the second portion being configured to exert a second force in a second direction, the first and second directions forming an angle with respect to each other.

14. An apparatus comprising:
   an intramedullary member;
   a fixation plate having a first bone-engaging surface configured to contact a first exterior bone surface; and
   a structure adapted to maintain the first bone-engaging surface in contact with the first exterior bone surface, the structure including:
      a flexible elongate element adapted to extend and transversely through the intramedullary member;
      a coupling structure to operatively couple the elongate element and the fixation plate at an end portion of the elongate element; and
      an anchor operatively coupled to the elongate element at an opposite end portion of the elongate element, the anchor having a second bone-engaging surface configured to contact a second exterior bone surface remote from the first exterior bone surface, wherein the anchor is configured to extend transversely through the intramedullary member while in an insertion configuration, and wherein the elongate element cannot be removed through the intramedullary member while the anchor is in an anchoring configuration,
      wherein the coupling structure includes a ferrule configured to be crimped to the end portion of the elongate element and the anchor comprises a further coupling structure including a ferrule configured to be crimped to the opposite end portion of the elongate element.

15. The apparatus of claim 14, wherein the first bone-engaging surface is shaped to approximately match an exterior bone surface of a fibula.

16. The apparatus of claim 15, wherein the second bone-engaging surface is shaped to approximately match an exterior bone surface of a tibia.

17. The apparatus of claim 14, wherein:
the fixation plate and the anchor are oriented so that the first and second bone-engaging surfaces face approximately toward each other; and
the ferrule is crimped to the end portion of the elongate element on a side of the fixation plate remote from the further ferrule.

* * * * *